United States Patent [19]
Lönnö

[11] Patent Number: 6,079,351
[45] Date of Patent: Jun. 27, 2000

[54] WETTING INDICATOR FOR COMPOSITES

[76] Inventor: Anders Lönnö, Holländargatan 9A, S-111 36 Stockholm, Sweden

[21] Appl. No.: 08/894,083
[22] PCT Filed: Feb. 13, 1996
[86] PCT No.: PCT/SE96/00187
    § 371 Date: Aug. 13, 1997
    § 102(e) Date: Aug. 13, 1997
[87] PCT Pub. No.: WO96/25655
    PCT Pub. Date: Aug. 22, 1996

[30] Foreign Application Priority Data

Feb. 13, 1995 [SE] Sweden ................... 9500513

[51] Int. Cl.$^7$ .............. G01K 1/02; G01K 11/00
[52] U.S. Cl. ............. 116/206; 116/217; 374/160; 374/161
[58] Field of Search ................. 116/200, 201, 116/206, 207, 212, 217, 218, 219, DIG. 7, 216; 374/160, 161, 162; 252/962; 436/164; 422/55, 231, 232

[56] References Cited

U.S. PATENT DOCUMENTS

| 3,759,261 | 9/1973 | Wang | 116/200 |
| 4,280,441 | 7/1981 | McNeely | 116/217 |
| 4,333,339 | 6/1982 | McNeely et al. | 116/217 |
| 4,428,321 | 1/1984 | Arens | 116/217 |
| 4,846,095 | 7/1989 | Emslander | 116/206 |

OTHER PUBLICATIONS

Chemical Abstracts, vol. 113, 1990, Dec. 3, No. 23 Defect Detection in Carbon Fiber Composite Structures by Magnetic Resonance Imaging, Jackson P. et al.

Primary Examiner—Andrew H. Hirshfeld
Attorney, Agent, or Firm—Jacobson, Price, Holman & Stern, PLLC

[57] ABSTRACT

The invention relates to a device for obtaining, in the manufacture of a high-strength composite, an indication the reinforcement layer of the composite has been wetted throughout by the matrix material of the composite. The reinforcement layer is of the type which mainly consists of fibers or fiber bundles which do not become translucent or transparent when wetted by the matrix material, such as carbon or aramide fibers or fiber bundles. The matrix material of thermosetting plastic is applied in a liquid state in the manufacture according to, for instance, the technique of hand lay-up. The reinforcement layer includes indicating fibers which become translucent or transparent when wetted by the matrix material. A good indication is obtained if the indicating fibers have such properties that they become translucent only when the adjoining reinforcing material has been completely wetted throughout. Preferably the indicating fibres are uniformly distributed across the reinforcement layer and in an amount that does not affect the properties of the composite significantly.

16 Claims, 2 Drawing Sheets

WETTING INDICATOR FOR COMPOSITES

BACKGROUND OF THE INVENTION

1. Technical Field of the Invention

The invention relates to a device for indicating that a reinforcing material, which is made of fibers and included in a composite material and which does not become translucent or transparent in wetting, has become wetted throughout by the matrix of the composite material while making the composite material. The device can indicate, for instance, that the carbon fiber reinforcement for the material of a hull or the like has been completely wetted throughout by liquid thermosetting plastic in the manufacture of the hull.

2. Description of the Related Art

An object of a composite material can be made by the material, which contains a reinforcement and a matrix that is liquid at certain stages of the manufacture, being supplied to a mould where the object obtains its shape when the matrix sets. Depending on whether the mould is of the type having a cavity or only a surface determining the shape of the object, the shape will be substantially determined by all its surface portions or only the inside or outside of the object. When manufacturing e.g. hulls of reinforced thermosetting plastic, moulds determining only the outer surface of the hull, so-called female moulds, are used in most cases.

One technique of manufacturing hulls is laminating by hand lay-up. The fibre reinforcement consisting of cut-out parts of a fabric or mat is arranged on a layer of liquid plastic which has been rolled on with a roller onto the mould surface. The reinforcement is then worked with a soft roller or brush so as to be impregnated and wetted with plastic. Finally, air and excess plastic are pressed out by means of a metal roller from the layer and the space between the layer and the underlying surface. Moreover, minor inclusions of air that are bound to the surfaces of the reinforcing fibres are removed. Owing to such working, wetting is further improved. The entire surface of each fiber of the reinforcement will then be substantially completely coated with matrix material.

To this first layer, additional layers are applied, as described above for the first layer. For large objects, use can be made of intermediate curings when making the laminate. Otherwise, all the layers can be applied in succession, curing taking place after application of the last layer.

After the application of each layer, it is necessary to make sure that the reinforcement of the layer has been properly wetted throughout. If the composite material should contain inclusions of air or voids, the hull will have an inferior quality with a risk of inferior strength since the composite can delaminate adjacent the inclusions of air and water can diffuse in the inclusions and cause chemical degradation of the material and cracking by frost. Insufficient wetting also reduces the resistance to compression of the composite, which may cause breaking of the hull.

For high-strength composite materials, a reinforcement consisting of practically merely carbon fibres or aramide fibers or a mixture thereof has recently come into use. The drawback of these materials is that it is difficult to visually form an opinion whether they have become well wetted throughout. To make sure that the wetting has been sufficient, ultrasonic testing and other testing techniques have been applied, which has contributed much to these composites being very expensive. The fact that the manufacture must be particularly precise owing to the lack of easy checking has also contributed to the increased cost.

BRIEF SUMMARY OF THE INVENTION

The object of the invention is to provide a device as mentioned in the introduction and having the following properties:

When manufacturing composite materials, it should be easy to make sure whether a reinforcing material has been well wetted throughout. This applies to reinforcing fibres in e.g. high-strength composite materials, the wetting of which has previously been difficult to estimate.

It should be possible to carry out the inspection in a short time and without expensive and complicated equipment.

The object is achieved by the device having the features as defined in the appended claims.

According to the invention, it is suggested that, intermixed with the reinforcing material, elements are added which have the same wetting properties as the reinforcing material, preferably as fibers in the form of threads, bundles, flakes, wads or the like of a material which becomes translucent or transparent by a shade of colour that depends on the nature of the material when its surface has been wetted by the matrix material. This indicating material, which preferably should also serve as reinforcement, should be added in an amount that is relatively small, such that the properties of the composite material are not changed to an unacceptable extent, but yet sufficient to obtain a good indication. The amount, which in the preferred embodiment is selected to be 4%, should in normal applications be less than about 5%. The elements added should be uniformly spread in the reinforcing material in such a manner that if they have all become wetted throughout, it can be assumed that the reinforcing material in the areas round the elements has also become wetted. The distances between the elements should not be chosen to be greater than to make these surrounding areas together cover the entire reinforcing material. Mixed reinforcements containing e.g. carbon fiber and glass fibre materials are already available, but the purpose of these reinforcements is to obtain other properties or a less expensive reinforcement. The admixture of glass fibers therefore is much greater, about 50%, as compared with reinforcements according to the present invention.

The reliability of the indication will be improved if the elements have such properties that they will be translucent/transparent only when the adjoining reinforcing material has become completely wetted throughout. These properties can be affected by the choice of the material of the elements and surface treatment.

When the composite material is a reinforced thermosetting plastic intended for hulls, use is often made of ester plastic or epoxy plastic as matrix material. In their liquid state, these materials are transparent in ordinary light. The indicating elements may then consist of certain polymers or glass fiber materials which from being, for instance, white in dry state become translucent or transparent when wetted. They will then let through the colour of the base, which can be the colour of the gel coat or the black colour of the subjacent carbon fibre reinforcement. Of course, a colour of the elements should be selected that is different from that of the base in order to obtain a clear change of colour. For other matrix and indicator materials, it may be necessary to use a light of a different wave range, for instance, the fluorescence from elements that have become wetted can be used for indicating purposes.

Reinforcing materials of carbon fibers often are in the form of a fabric or a stiched so-called multiaxial mat. The warp and weft threads of the fabric consist of flat bundles of a large number of carbon fibers or fibrils. The mat, which is used if a more rigid composite having a higher fiber content is desired, may consist of two plies, each comprising parallel threads of the same type as those used in the fabric. The threads of the various plies are allowed to be oriented in different directions. When two plies are used, the threads of the second ply are often directed perpendicular to the threads of the first ply. For fixing the threads, seams are made through the plies. A reinforcement of aramide fibers is carried out in a similar manner.

According to the invention, it is further suggested that a fabric or mat comprises, as elements, threads or bundles of the above-mentioned material, which is suitable for indicating. By using such threads of a colour contrasting with that of the reinforcing material, such as a bright colour in the black carbon fiber material, they will be easy to spot in inspection. The threads, which can have the same thickness as the threads of the reinforcing material, are inserted preferably at the same distance from each other in the warp and in the weft as well as in both plies or all plies. This distance should give the elements a spreading in the reinforcing material that, as stated above, is determined by the used materials, the type of composite, the manufacturing technique etc.

When indicating threads, which become translucent or transparent when wetted, are inserted in both the warp and the weft and in the two plies of the mat, spots arise where the threads intersect, i.e. parts of the built-up layer which, when wetted, become translucent or transparent throughout the layer. If more than two plies are used in a mat, the indicating threads are arranged in the additional plies, such that they extend in the above-mentioned spots or restricted parts. In this manner, indication is obtained throughout the layer. As a result, it is possible to make sure that the layer has been wetted throughout its thickness, not only in its uppermost ply.

If the layers include a reinforcing fabric or mat having threads or bundles in one ply only, the reinforcement is usually laid with the threads oriented in different directions in the layers. In the intersection of indicating threads, spots for indicating in two layers will be obtained.

The invention is not restricted to manufacture by simple hand lay-up. It can also be used in vacuum infusion using a transparent coating foil and for preimpregnated reinforcing materials, the wetting being checked before manufacturing the composite object.

According to the invention, it is possible to have a quality control of e.g. high-strength composite materials with reinforcement of carbon fibers and aramides. The appearance of these materials does not change when wetted, and therefore it has previously been necessary to use time-consuming and expensive techniques.

The device according to the invention causes an indication in depth throughout the layer last applied, in some cases throughout the thickness of the entire applied material.

The inspection can be carried out more systematically since a checked pattern or the like is available for assistance.

It is possible to avoid expensive preparation of the carbon fiber material, which is often regarded as necessary for complete wetting, such as preimpregnation and subsequent cold storage to prevent the curing of the impregnation.

BRIEF DESCRIPTION OF THE DRAWINGS

A preferred embodiment will be further described with reference to the accompanying drawings.

DETAILED DESCRIPTION OF THE INVENTION

Figure 1:
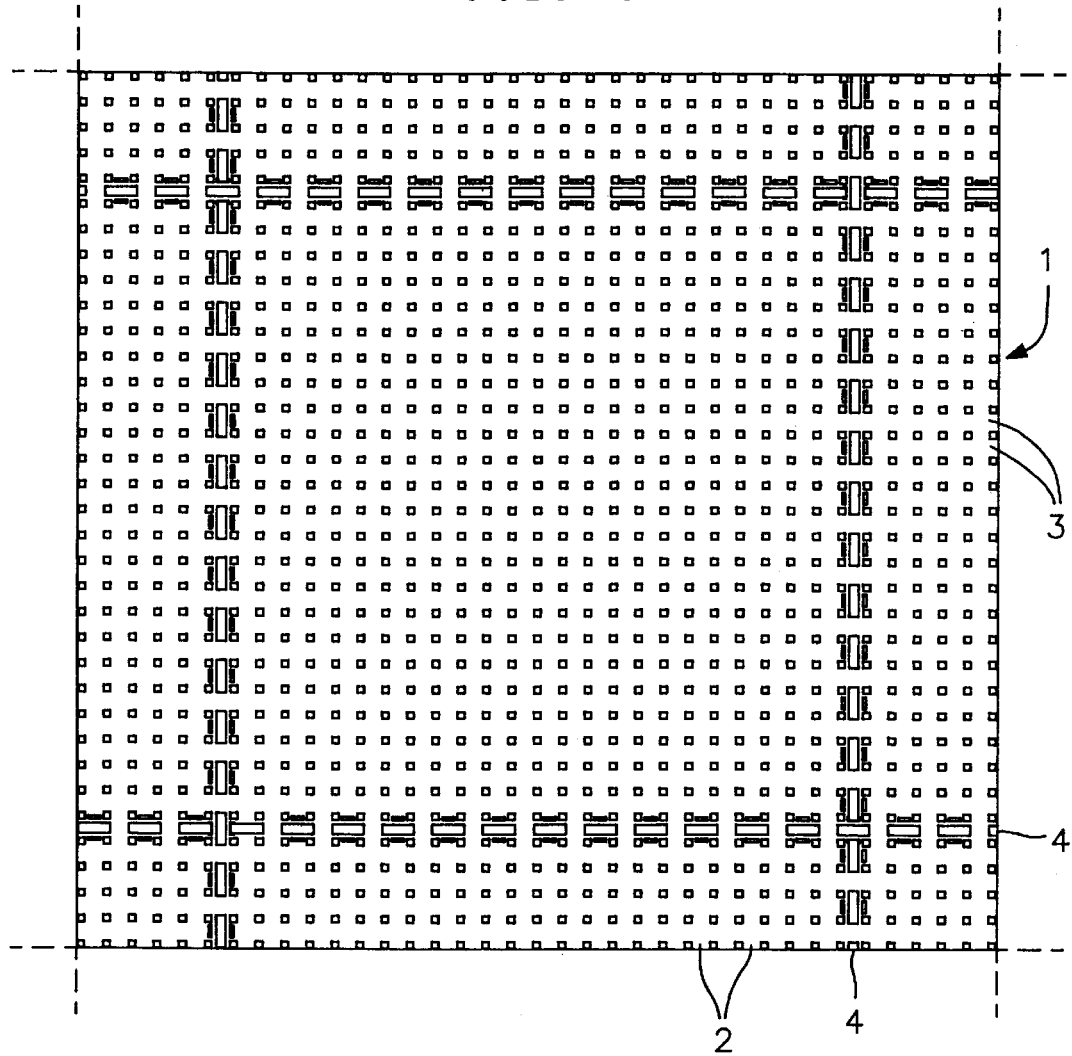
FIG. 1 shows a reinforcing material in the form of a fabric containing elements according to the invention.

FIG. 1 illustrates a portion of a plain weave fabric 1 to be used as reinforcement in a composite. The fabric, which is of standard type with the exception of the inserted indicating elements which will be described below, comprises bundles of the same type for both the warp 2 and the weft 3 of the fabric. The bundles are of an ordinary kind and are elongate in cross-section having a height which is small in relation to the length and consist of a large number of parallel longitudinal fibers of fibrils of carbon fiber. Instead of every twenty-fifth carbon fiber bundle in warp as well as weft, indicating elements 4 in the form of bundles of glass fibers are inserted. In the preferred embodiment, these bundles are of a cross-section corresponding to that of the carbon fiber bundles so as to prevent the thickness of the fabric from being irregular. The ratio of 4% of the amount of indicating material, glass fibers, to the amount of reinforcing material, carbon fibers and glass fibers, has been selected empirically. In other types of fabrics, other ratios can be selected. If narrower bundles of glass fibers are used, the ratio can, of course, be reduced to, for instance, 2.5% which in respect of strength is more favourable, or the distance between the glass fiber bundles can be reduced at the same ratio. This ratio should not be so great that the reinforcement is impaired in an impermissible manner. Also the manufacturing technique is of importance. If, for instance, during application, the layers are worked more between the bundles than on the bundles, the ratio can be decreased without the risk of error in indication being unacceptable.

Figure 2:
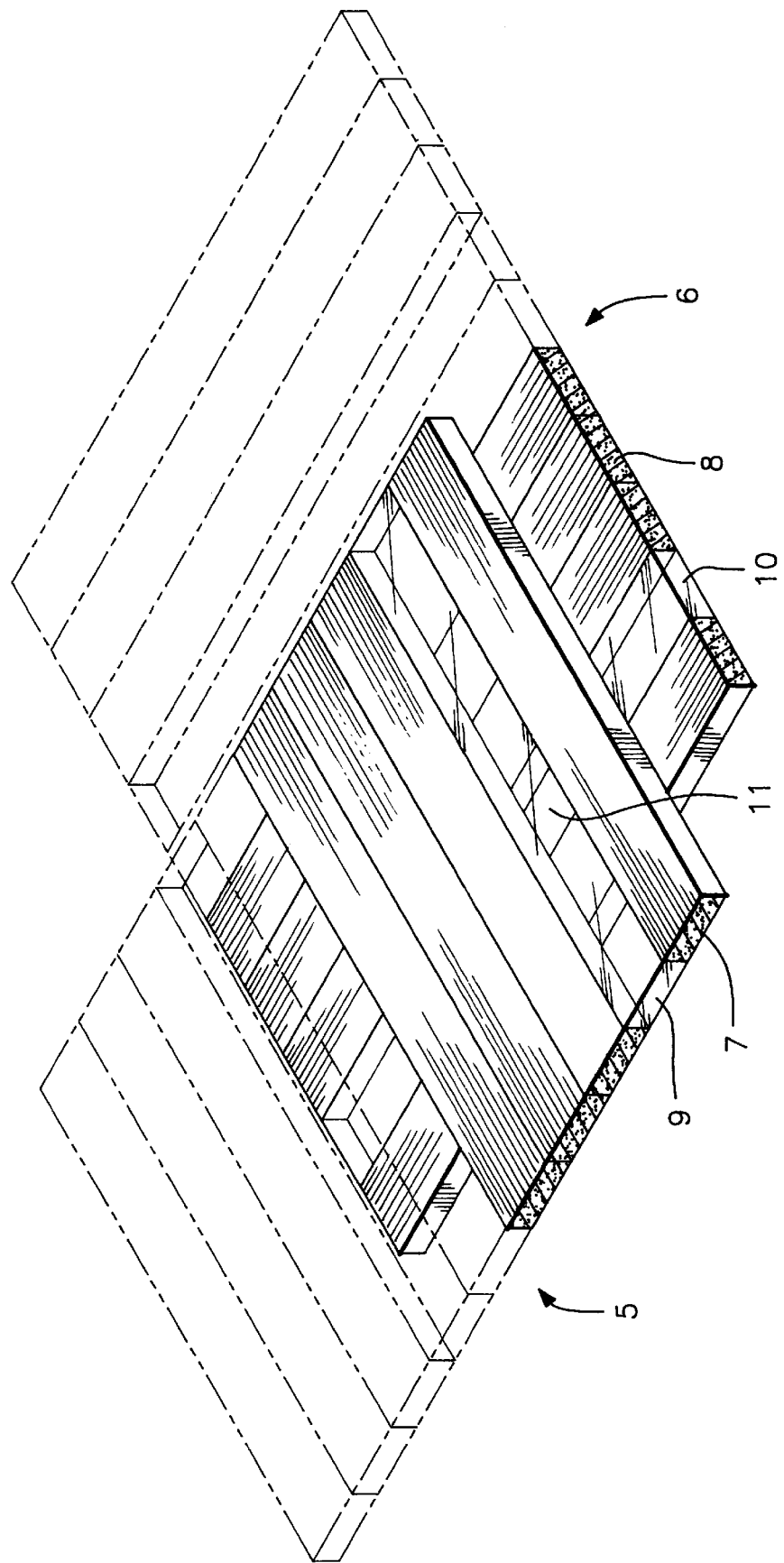
FIG. 2 shows a reinforcing material in the form of a two-ply mat.

FIG. 2 illustrates a reinforcing material of reinforcing fibers, such as carbon fibers or aramide fibers, in the form of a multiaxial mat. The mat, as illustrated, consists of two plies generally designated by the reference numerals 5 and 6. Each ply comprises parallel threads of the same type as those used in the fabric. The threads 7 of the first ply 5 are oriented in a different direction from the threads 8 of the second ply 6. The threads 7 and 8 consist of flat bundles of a large number of fibers or fibrils. When two plies are used, the flat bundles or threads 8 of the second ply 6 are often directed perpendicular to the threads 7 of the first ply 5. For fixing the threads, seams can be made through the plies.

Interspersed and aligned with the threads 7 and 8 are similar threads or bundles of indicating fibers 9 and 10, respectively. The indicating threads are of a color contrasting with that of the reinforcing material, such as a bright color in the black of a carbon fiber material, so that the indicating fibers will be easy to spot upon inspection. The indicating bundles 9 and 10, which can have the same thickness as the bundles 7 and 8 of the reinforcing material, are inserted preferably at the same distance from each other in both plies, if two, or in all plies if more than two. This distance should give the elements a spreading in the reinforcing material that, as stated previously, is determined by the used materials, the type of composite, the manufacturing technique, etc. With the indicating threads inserted in both plies of the mat, spots 11 arise where the threads 9 and 10 intersect upon becoming translucent or transparent when wetted.

The manufacture of composite is carried out in the same manner whether the reinforcing material comprises elements according to the invention or not. However, the inspection after application of each layer is effected more systematically by making sure that all the fiber glass threads and especially their intersections have changed from the original colour to a colour which depends on, inter alia, the base of the previously applied layer.

I claim:

1. A composite containing a matrix material of a thermosetting plastic and a reinforcement layer, the reinforcement layer having a plurality of elongated reinforcing fibers, wherein said reinforcing fibers do not become translucent when wetted by said matrix material, said reinforcing fibers including at least a first series of fibers and a second series of fibers, said reinforcing fibers of said first series of fibers being generally aligned in a first direction, said reinforcing fibers of said second series of fibers being generally aligned in a second direction different from said first direction so that said first series of fibers crosses said second series of fibers, wherein the improvement comprises:

a plurality of indicating fibers, at least one of said indicating fibers being generally aligned and substantially planar with said reinforcing fibers of at least one of said first and second series of fibers, said indicating fibers becoming translucent when wetted by the matrix material, said indicating fibers being present in such small quantity that the properties of the composite are not significantly different from the properties of a composite containing only reinforcing fibers.

2. The composite as claimed in claim 1, wherein the indicating fibers are uniformly distributed across the reinforcement layer.

3. The composite as claimed in claim 1, wherein the indicating fibers are made of a reinforcement material, so that the indicating fibers reinforce the composite.

4. The composite as claimed in claim 3, wherein the reinforcement material of the indicating fibers is selected from the group consisting of glass and polymer.

5. The composite as claimed in claim 1, where in the volume of the indicating fibers is a maximum of about 5% of the total volume of said reinforcing fibers and said indicating fibers.

6. The composite as claimed in claim 5, wherein the volume of the indicating fibers is about 4% of the total volume of the reinforcing fibers and the indicating fibers.

7. The composite as claimed in claim 1, wherein the reinforcement layer includes a fabric, the first series of fibers is a warp, the second series of fibers is a weft, and the warp and weft interweave to form the fabric.

8. The composite as claimed in claim 7, wherein said at least one indicating fiber is included in the warp of the fabric, and at least one additional indicating fiber of said indicating fibers is included in the weft of the fabric, and that the fabric is so arranged that the at least one and the at least one additional indicating fibers form an intersection which, when wetted, becomes translucent throughout the fabric.

9. The composite as claimed in claim 1, wherein the reinforcement layer includes a mat, and each of the first and second series of fibers is a mat ply.

10. The composite as claimed in claim 9, wherein the at least one indicating fiber is inserted in one of the mat plies, and at least one additional indicating fiber of said indicating fibers is inserted in the other of the mat plies, wherein the at least one and the at least one additional indicating fibers form an intersection which, when wetted, becomes translucent throughout the mat.

11. The composite as claimed in claim 1, wherein the indicating fibers become transparent when wetted by the matrix material.

12. The composite as claimed in claim 1, wherein the reinforcing fibers are selected from the group consisting of carbon fibers and aramide fibers.

13. The composite as claimed in claim 1, wherein the volume of the indicating fibers is at least 2.5% of the total volume of the reinforcing fibers and the indicating fibers.

14. A composite containing a matrix material of a thermosetting plastic and a reinforcement layer, said reinforcement layer comprising:

a plurality of elongated reinforcing fibers, wherein said reinforcing fibers do not undergo a color change when wetted by said matrix material, said reinforcing fibers including at least a first series of fibers and a second series of fibers, said reinforcing fibers of said first series of fibers being generally aligned in a first direction, said reinforcing fibers of said second series of fibers being generally aligned in a second direction at an angle to said first direction;

a plurality of indicating fibers, said indicating fibers undergoing a color change when wetted by the matrix material, at least one of said indicating fibers being generally aligned with said reinforcing fibers of said first series of fibers, at least one additional indicating fiber of said indicating fibers being generally aligned with said reinforcing fibers of said second series of fibers, said at least one and said at least one additional indicating fibers crossing one above the other, the volume of said indicating fibers being up to about 5% of the total volume of said reinforcing fibers and said indicating fibers.

15. The composite as claimed in claim 14, wherein the reinforcement layer includes a fabric, the first series of fibers is a warp, the second series of fibers is a weft, and the warp and weft interweave to form the fabric.

16. The composite as claimed in claim 14, wherein the reinforcement layer includes a mat, and each of the first and second series of fibers is a mat ply.

\* \* \* \* \*